(12) United States Patent
Castillo et al.

(10) Patent No.: US 8,746,964 B2
(45) Date of Patent: *Jun. 10, 2014

(54) FLEXIBLE BAG AND MIXING SYSTEM WITH RIGID CONTAINER

(75) Inventors: Jose Castillo, Brussels (BE); Florence Bosco, Mignault (BE)

(73) Assignee: Artelis S.A., Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/615,746

(22) Filed: Sep. 14, 2012

(65) Prior Publication Data

US 2013/0121104 A1 May 16, 2013

Related U.S. Application Data

(63) Continuation of application No. 12/444,049, filed as application No. PCT/EP2007/054000 on Apr. 24, 2007, now Pat. No. 8,292,491.

(30) Foreign Application Priority Data

Oct. 3, 2006 (EP) .................. PCT/EP2006/066980
Apr. 12, 2007 (EP) .................. PCT/EP2007/053595

(51) Int. Cl.
*B01F 13/08* (2006.01)

(52) U.S. Cl.
USPC .......................................... 366/273

(58) Field of Classification Search
USPC ........................................... 366/273
See application file for complete search history.

(56) References Cited

U.S. PATENT DOCUMENTS

2004/0190372 A1* 9/2004 Goodwin et al. ............. 366/273
2005/0002274 A1* 1/2005 Terentiev ..................... 366/273
2007/0253287 A1* 11/2007 Myhrberg et al. ........... 366/273

* cited by examiner

*Primary Examiner* — Walter D Griffin
*Assistant Examiner* — Christopher Vandeusen
(74) *Attorney, Agent, or Firm* — King & Schickli, PLLC

(57) ABSTRACT

Flexible bag includes at least a first wall, a second wall facing the first wall when the flexible bag is folded and a functional part having at least a portion protruding from the first wall inside the bag. The second wall includes protective means intended to prevent damage to the flexible bag and/or to the functional part.

20 Claims, 2 Drawing Sheets

FLEXIBLE BAG AND MIXING SYSTEM WITH RIGID CONTAINER

Figure 1:
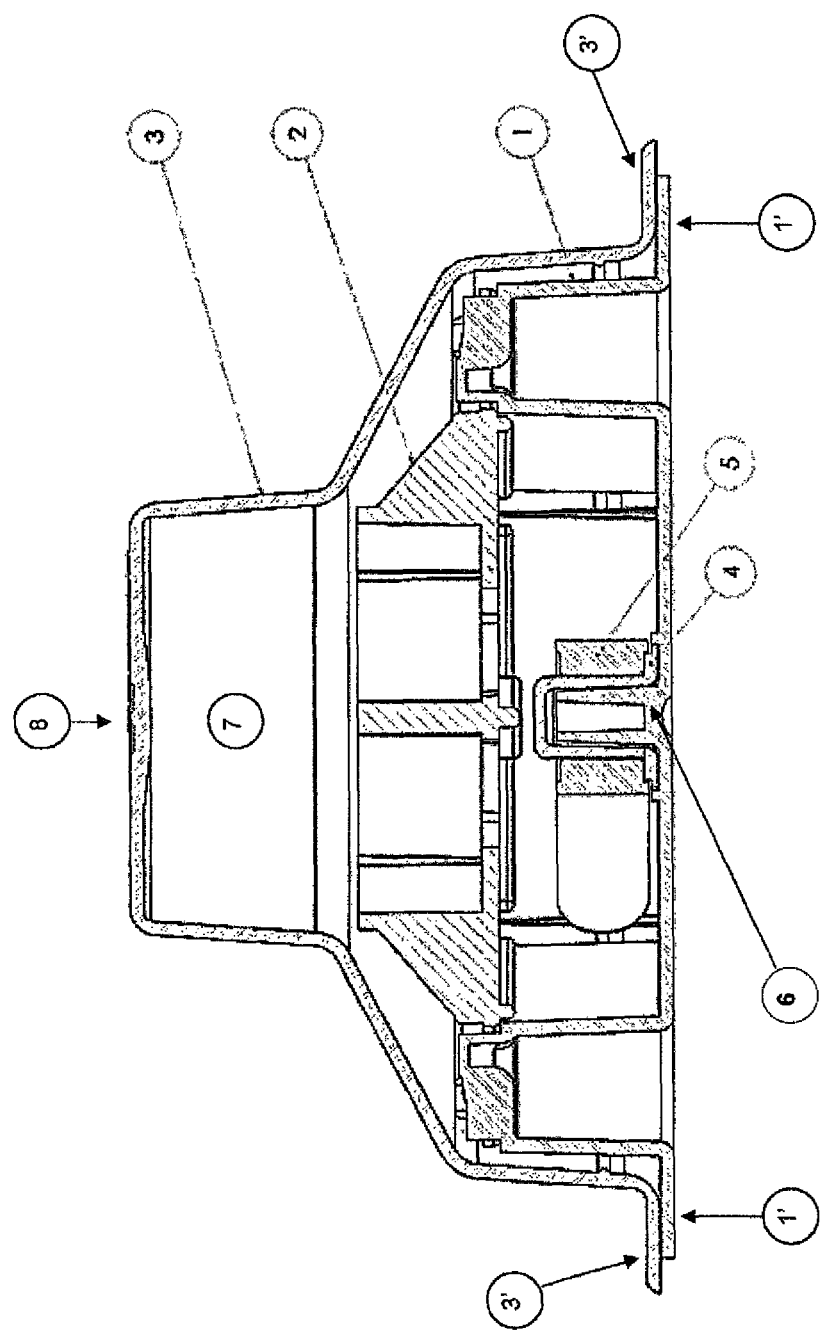

This application is a continuation of U.S. patent application Ser. No. 12/444,049, filed on Apr. 2, 2009, the disclosure of which is incorporated herein by reference.

The present invention relates to a flexible bag; to a mixing system comprising such a flexible bag and to a method for fixing a specific flexible bag into a rigid container.

The storage, mixing and/or suspension of solutions is required in many technical fields such as biotechnology, pharmaceuticals and medical.

For example, in the field of the biotechnology and pharmaceutical industry, it is often necessary to prepare and to complement solutions, buffers, culture medium, suspensions, etc (referred to in general terms hereinafter as liquid substances) and to store these solutions. Some specific applications include dilution, dissolution and/or adjusting and/or measuring pH, salinity conditions, concentration, osmolality, temperature . . . of a liquid substance of any kind (buffer, culture medium, saline solution, etc.)

To be safe and effective for their intended use, solutions of culture media, buffers, reagents, etc. used in these fields must be pure and sterile. Accordingly, the mixing tank, mixing device, storage bag and all other reusable components that contact the solution must be carefully cleaned after use to avoid any cross contamination with subsequent batches of solutions. The cleaning of the structural components is labour-intensive, time-consuming, and costly.

In order to avoid these cleaning steps, single use flexible bags have been developed. These are disposable flexible bags intended to be supported in rigid containers and provided with functional parts like a mixing device, sensors, dip tubes . . . and generally intended to be supported in a rigid container. Advantageously, the mixing devices used in these bags are magnetic devices driven by an external driver positioned outside of the bag and may be part of or fixed to the rigid container. By doing so, there is no risk of contamination of the contents of the bag from the outside.

However, such mixing device and other functional parts generally protrude inside the bag so that in the case said bag has a flexible wall facing the protruding part, said wall can be damaged by the protrusion before it is filled.

Besides, in some circumstances, inserting the flexible bag into a rigid container is not easy namely because said bag is not easy to handle and/or because some parts must be connected with parts of the container.

Finally, some functional parts are not fixed inside the bag so that they need to be kept in place during shipping and handling of the bag when it is empty.

The present invention aims at solving these problems by providing a system where the flexible bag is prevented from being damaged by a part protruding inside of it; where if said part is not fixed to the bag, it is kept in place during storage and handling of the empty bag; and where said bag is easier to install inside a rigid container.

Accordingly, the present invention relates to a flexible bag comprising at least a first wall, a second wall facing the first wall when the flexible bag is folded and at least one functional part having at least a portion protruding from the first wall inside the bag, wherein the second wall comprises protective means intended to prevent damage to said flexible bag and/or to said functional part.

According to the invention, the terms "flexible bag" designate a bag or pouch made of walls of similar structure preferably assembled by welding. These walls may be made of a mono- or multilayer film including or not a barrier layer based on a barrier polymer like EVOH (ethylene vinyl alcohol polymer). Generally, these films may have an inner layer (in contact with the contents of the bag when filled) based on a polyolefin, preferably an ULDPE (ultra-low density polyethylene, pref. medical grade).

The bag may be of cylindrical shape although cylindrical flexible bags are not easily baffled and difficult to manufacture. A bag with a cubic or parallel-piped shape is preferable namely because it works as a baffled tank which enhances its mixing capacity.

The flexible bag according to the present invention comprises at least two facing walls. This means in fact that when said bag is empty, at least two portions of its wall(s) are in contact with each other by their internal surface i.e, their surface intended to be in contact with the contents of the bag.

The flexible bag according to the invention may be used to store, mix, handle (for any purpose whatsoever) a fluid. According to the invention, it has a functional part having at least a portion protruding inside of it i.e. extending in the volume defined by the bag's wall(s). This part is protruding from a wall of the tank. This is meant to encompass the cases where the part would be protruding from an angle and potentially damaging an opposite wall or angle. Also, the part must not necessarily by fixed on said wall or corner. It might merely rest on it or pass through an opening therein. If it is fixed to it, it may be by welding, riveting, clamping . . . .

This protruding functional part may be any accessory required for at least one active function of the bag. The functional part is preferably chosen between a mixing device; a gas sparger; a dip tube; or a sensor for measurement of temperature pH, conductivity, turbidity, biomass, redox potential, dissolved oxygen or any other signal.

Although this accessory may have any shape or size, the present invention is advantageously applied to large parts so that the protective means can fulfill several functions as will be explained later on. By "large" is meant having their biggest dimension in the range of the centimeters (e.g. up to 30 cm).

For instance, the present invention gives good results when the functional part is a mixing device which may either be a mere impeller protruding inside the bag or a more sophisticated system like the mixing dish from the HYCLONE MIX-TAINER Bioprocessing System or the LEVTECH Disposable Mixing System, or even a combination of a mixing device and gas sparger, or any other part combining a mixing effect with another function.

Although any kind of mixing device may be used in a flexible bag, it is preferably a device including a magnetic impeller which is driven from the outside as explained above.

The present invention gives good results when the mixing device comprises a rotary magnetic impeller located in a compartment delimited by a wall, said mixing device further comprising:
  at least one liquid inlet opening located in a central area of the wall;
  at least one liquid outlet opening located in a peripheral area of the wall; and
  deflecting means that substantially alter the natural rotational direction of the liquid exiting the outlet opening.

These deflecting means and/or the wall of this mixing device might indeed comprise angles or other kinds of prominent parts which are susceptible to damage the wall of the bag facing said mixing device.

Besides, as set forth in a co-pending application, said mixing device is not necessarily secured to the bag when said bag is shipped and handled before use so that the cover of the invention may help (together with the vacuum generally applied to said bag) keeping said part substantially at the place where it should be fixed in use.

If said mixing device is secured to the bag, it may be by welding or by using at least one of the following:
- magnets in extension arms susceptible to work with corresponding magnets disposed in the rigid container;
- at least two extension arms welded (or mechanically fixed in any other way) to at least two drains or two other rigid components of the bag.

The flexible bag according to the present invention comprises protective means on the wall (or the corner: see previously) opposite to the one where the functional part is located. These protective means may be integral with the bag's wall (for instance: they may consists in a part of the wall being of higher thickness) or they may be fixed to it. These protective means are preferably secured to the wall of the bag and even more specifically, they are preferably secured to an opening of said wall and more precisely: they are preferably welded or clamped on the periphery of the opening.

These means may be of any geometry allowing them to protect the protruding portion of the functional part. Preferably, they are in the shape of a cover having a cavity sized to accommodate the protruding portion of the functional part. Preferably, said cavity has a shape substantially matching the external shape of the protruding portion. The lower border of said cover is preferably secured from the inside (welded, clamped or fixed by any other means) to the periphery of said opening i.e. on the inner surface of the bag in order to avoid that the outer layer of the film would be in contact with the liquid. Nevertheless, it can be also secured from the outside of said periphery. In that embodiment, said securing is preferably performed before the final assembly of the bag.

In order to achieve leak tightness, the cover is preferably either welded or clamped (using a flange and a gasket) on the periphery of the opening.

Welding the cover to the outer periphery of the opening is preferred. To that end, said cover is preferably provided with a welding flange located at its periphery. In the case the functional part also comprises a welding flange, both flanges are preferably of a size and shape such that the flange of the cover rests on the flange of the functional part when the bag is empty. This allows a good distribution of the pressure between both flanges when the bag is positioned inside a rigid container.

To ensure the welding ability of the cover on the bag, said cover is preferably based on a material compatible with the material constituting the outer surface of the bag. Considering the layout of the industrial films set forth above, a polymer of ethylene is a good choice. Preferably, a HDPE (high density polyethylene) is used because other polymers like EVA (Ethylene Vinyl Acetate copolymer) or LDPE are not rigid enough.

This cover may be obtained by any method suitable for moulding plastic parts, preferably by injection moulding. Hence, injection moulding grades of the above mentioned polymers (more preferably: of HDPE) am preferably used.

The cover according to this embodiment of the invention comprises a cavity which is substantially matching the external shape of the protruding portion of the functional part. The terms "substantially matching" means in fact that the protruding portion fits (can be inserted) inside the cover and can be removed there from i.e. that it has smaller dimensions and an adequate shape to be able to be received (preferably completely) inside the cover.

In one embodiment, the protruding portion of the functional part does not fit tightly inside the cover so that there is no wear between the surfaces of both parts (except perhaps on their welding flanges or other substantially horizontal contact surface, if any) and this even with the usual manufacturing tolerances.

However, when the cover is used to fix the protruding part to a rigid container (or any other support/part), it may be preferable to fit both pieces more tightly at least on a portion thereof so that a torque exerted on the cover can easily be transmitted to the protruding portion of the part. In that embodiment, corresponding portions in relief may be provided on both parts which are in contact when the cover rests on the protruding portion of the functional part so that the torque transmission is improved.

Generally, the cover has a substantially constant wall thickness which depends on the mechanical resistance required.

As to its outer shape, it may be adapted to enhance the ease of handling of the bag and/or the fixation of the protruding part on a support. In that regard, it may be provided with an extension and/or its cavity may be extended upwards so that it acquires a prehensile shape.

The protective means of the bag according to the invention may be equipped with functional means for instance: with port(s) for entry/exit of liquid(s) or gas; with sensors or supports there for; with impeller(s) which may be lowered inside the bag once filled . . . .

This functional means must of course be disposed/fixed on said means in a way such that they still allow the means to exert their protective function (i.e. allow the protruding portion to fit in the cavity of the cover, the case being).

The present invention also concerns a mixing system comprising a flexible bag as described above and a rigid container supporting said bag.

Preferably, according to that aspect of the invention, the functional part is a magnetic mixing device and the mixing system comprises a magnetic driver located outside the container, generally below its bottom.

In that embodiment, preferably, a portion of the flexible bag is sandwiched between at least a portion of the mixing device and a portion of the rigid container, these portions being generally part of the bottom wall of the bag and of the rigid container respectively. "Sandwiched" means that said portions are directly in contact and pressed against each other by gravity (if the mixing device rests on the bottom of the mixing bag and the container) and/or by any other means which preferably do not perforate the bag and the container (additional magnets for instance).

There is hence no intermediate connecting piece between the mixing device and the driver, or, in other terms: there is no direct mechanical connection between both elements. Instead, either they are both precisely located relative to the rigid container (first embodiment) or they are free to auto align themselves through the magnetic forces they both exert on each other (second embodiment).

By doing so, there is no need to provide the bag and the container with an opening, no need to manufacture an additional connecting piece and the use of said containers can be made standard.

The present invention gives good results with the second embodiment mentioned above and especially, when the mixing device is not (at least not firmly) secured to the flexible bag so that the cover can help keeping said mixing device substantially in place during storage and handling of the empty bag. The vacuum generally applied on said bag also helps in that regard.

In order to allow the mixing device to auto align itself with its driver, the flexible bag of that embodiment may comprise a positioning mechanism to position and maintain the mixing device only approximately at a given location (i.e. said device is not secured to its walls but free to move a little relative to it) when the bag is inserted inside the rigid container This positioning mechanism may include welding tabs, bridges or any other fixation part (like a double annular wall for instance) fixed on the bag wherein the mixing device is retained but can move freely (relative to the bag) in at least one direction of space (and preferably, in the three directions of space) while remaining in a given perimeter (surrounding the driver when the bag is inserted in the rigid container).

This embodiment is advantageous because the mixing device will align itself automatically with its driver (through the magnetic forces they both exert on each other) so that there is no need for a perfect mechanical relative alignment between the mixing device, the driver and the rigid container. This embodiment is also advantageous because there is no need for the welding of a (potentially) large circumferential part, what presents quality issues as far as leakages are concerned.

As explained above, the protective means of the bag according to the invention may consist in a cover comprising a portion in relief cooperating with a matching portion in relief on the functional part so that said part can be fixed on the container using the cover.

Accordingly, the present invention also concerns a method for fixing a flexible bag as described above inside a rigid container, wherein the cover and the functional part bear complementary relieves and according to which the functional part is fixed to the container using the cover which is then decoupled from said part before filling the bag.

Figure 2A:
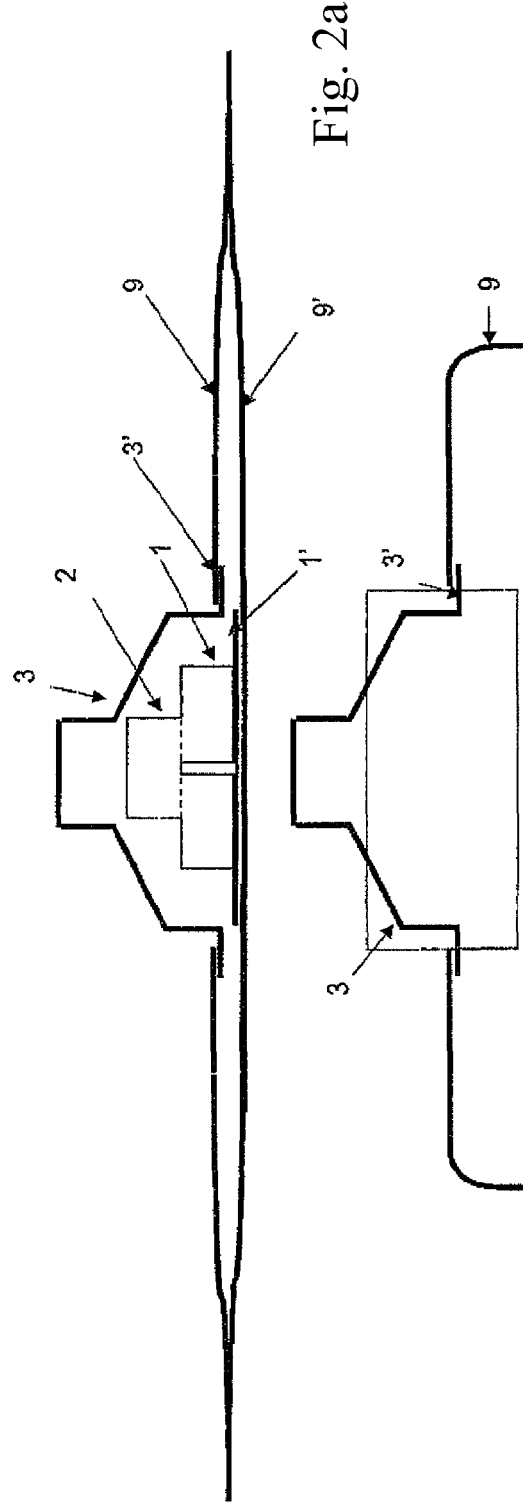
Figure 2B:
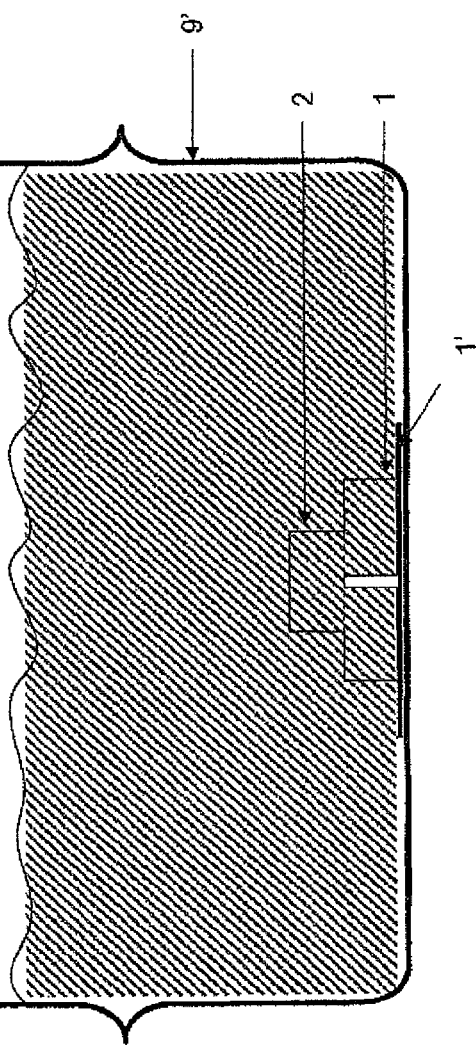

Other characteristics and advantages of the invention will appear more clearly in the light of the following description of a particular non-limiting embodiment of the invention, while referring to the figures attached (FIGS. 1, 2a, and 2b).

FIG. 1 shows in detail a mixing device inside the cavity of a protective cover, FIG. 2a, a schematic view of said mixing device and cover in an empty flexible bag and FIG. 2b in said bag filled with liquid.

FIG. 1 is an axial cut (i.e. a cut through a plane comprising the symmetry axis) through a mixing device (1, 2) provided with its protective cover (3). Both parts are provided with a welding flange (1', 3') intended to be welded on a flexible bag (not shown) respectively on the inner surface of the bottom wall (under surface of flange 1') and on the inner surface of the top wall, on the periphery of an opening there through (upper surface of flange 3').

The mixing device illustrated comprised a base (1), a cover (2) and a magnetic impeller (5) rotating on a bearing (4) supported by a protrusion (6) of the base (1).

The cover (3) has an internal volume or cavity substantially matching the external shape of the mixing device (1, 2) at its base but having a chimney or a dome shaped extension (7) at its top providing a grip enhancing the ease of handling of the cover and of the flexible bag for which it is intended. This extension can be used to integrate functional means, like ports for inlets or outlets of liquids or gases, probes, impellers or the like.

The cover (3) has been manufactured by injection moulding and it shows a substantially uniform wall thickness with just a slight increase in the neighbourhood of its injection point (8). It is made of an injection moulding grade of HDPE.

FIGS. 2a and 2b illustrate how the cover (3) is welded to the periphery of an opening into a bag comprising 2 facing walls (9, 9'), one of which (9) bearing a protective cover for the mixing device (1, 2) located on its facing wall (9). This welding is made between the upper surface of the cover's welding flange (3') and the inner periphery of the opening in the bag. It also illustrates how the mixing device is welded to the bottom of the bag (9') by the lower surface of its welding flange (1'), and how the 2 parts fit to each other when the bag is empty and are separate when the bag is empty, Although the preferred embodiments of the invention have been disclosed for illustrative purpose, those skilled in the art will appreciate that various modifications, additions or substitutions are possible, without departing from the scope and spirit of the invention as disclosed in the accompanying claims.

The invention claimed is:

1. A fluid processing apparatus comprising: a bag including first and second walls, said first and second walls at least partially defining an interior of the bag and being at least partially flexible; a mixer associated with the first wall; and a rigid cover Forming a part of the second wall, said cover arranged for preventing the mixer from contacting the flexible first and second walls when positioned adjacent to each other.

2. The apparatus of claim 1, wherein the second wall includes an opening therein, and wherein the cover is secured in the opening.

3. The apparatus of claim 2, wherein the opening includes a periphery and the cover includes a peripheral flange welded to the periphery of the opening.

4. The apparatus of claim 1, further including a base having a peripheral flange welded to the first wall, the base arranged for nesting with the rigid, cover.

5. The apparatus of claim 1, further including a driver for driving the mixer.

6. The apparatus of claim 1, wherein the mixer comprises a rotary mixer.

7. The apparatus of claim 1, wherein the mixer comprises an impeller.

8. The apparatus of claim 1, wherein the cover further comprises a port adapted for the addition or removal of material from the bag.

9. The apparatus of claim 1, wherein the cover projects vertically from a surface of the second wall.

10. The apparatus of claim 1, wherein the cover includes a sidewall connecting with a transverse wall.

11. The apparatus of claim 1, further including a base associated with the first wall for supporting the mixer.

12. The apparatus of claim 11, wherein the base comprises a bearing.

13. The apparatus of claim 11, wherein the base is at least partially elevated relative to the first wall, 14. The apparatus of claim 11, wherein the base comprises a protrusion for receiving the mixer.

15. The apparatus of claim 14, wherein the protrusion of the base extends into a cavity of the cover when the bag is collapsed.

16. The apparatus of claim 1, further including at least one of a port, a sparger, a sensor, and a sensor support.

17. The apparatus of claim 1, wherein the cover includes at least one of a port, a sparger, a sensor, and a sensor support.

18. The apparatus of claim 7, wherein the impeller comprises a magnetic impeller.

19. The apparatus of claim 11, wherein the base includes a welding flange welded to the first wall of the bag and the cover includes a welding flange welded to the second wall of the bag.

20. The apparatus of claim 1, wherein the cover at least partially receives the mixer.

* * * * *